(12) United States Patent
Caclin

(10) Patent No.: US 8,496,617 B2
(45) Date of Patent: Jul. 30, 2013

(54) BALLOON INFLATION DEVICE

(75) Inventor: Jérôme Caclin, Venissieux (FR)

(73) Assignee: Sedat, Irigny (FR)

( * ) Notice: Subject to any disclaimer, the term of this patent is extended or adjusted under 35 U.S.C. 154(b) by 204 days.

(21) Appl. No.: 12/274,815

(22) Filed: Nov. 20, 2008

(65) Prior Publication Data

US 2009/0227947 A1    Sep. 10, 2009

(30) Foreign Application Priority Data

Nov. 20, 2007  (FR) ...................................... 07 59171

(51) Int. Cl.
*A61M 29/00* (2006.01)

(52) U.S. Cl.
USPC .................................. 604/97.02; 604/100.03

(58) Field of Classification Search
USPC ................. 604/97.01–97.03, 100.01, 100.03, 604/98.01, 99.01–99.03, 96.01
See application file for complete search history.

(56) References Cited

U.S. PATENT DOCUMENTS

| | | | | |
|---|---|---|---|---|
| 4,370,982 A | * | 2/1983 | Reilly | 604/97.03 |
| 5,019,041 A | * | 5/1991 | Robinson et al. | 604/97.03 |
| 5,306,248 A | * | 4/1994 | Barrington | 604/97.02 |
| 5,470,317 A | * | 11/1995 | Cananzey et al. | 604/121 |
| 5,964,577 A | * | 10/1999 | Chuang | 417/63 |
| 6,063,057 A | * | 5/2000 | Choh | 604/99.01 |
| 6,394,977 B1 | * | 5/2002 | Taylor et al. | 604/100.03 |
| 2005/0056040 A1 | * | 3/2005 | Motush et al. | 62/292 |

* cited by examiner

*Primary Examiner* — Manuel A. Mendez
*Assistant Examiner* — Weng Lee
(74) *Attorney, Agent, or Firm* — Sughrue Mion, PLLC

(57) ABSTRACT

The balloon inflation device comprises a syringe (2) having a syringe barrel (4) and a syringe piston (6) slidably and rotatably movable. The piston (6) has an exterior threading. The syringe barrel also comprises a retractable mechanism (30) for retaining the piston (6) in the syringe barrel, which mechanism (30) is switchable between a retracted state in which the piston (6) is free to slide in the syringe barrel and an active state in which the free sliding of the piston (6) is impossible and in which the piston (6) can be screwed or unscrewed.

The device comprises a pressure gauge (104) for measuring the output pressure of the syringe barrel (4).

The pressure gauge (104) is mounted angularly movable with respect to the syringe barrel (4) and around the axis of the syringe barrel (4).

9 Claims, 9 Drawing Sheets

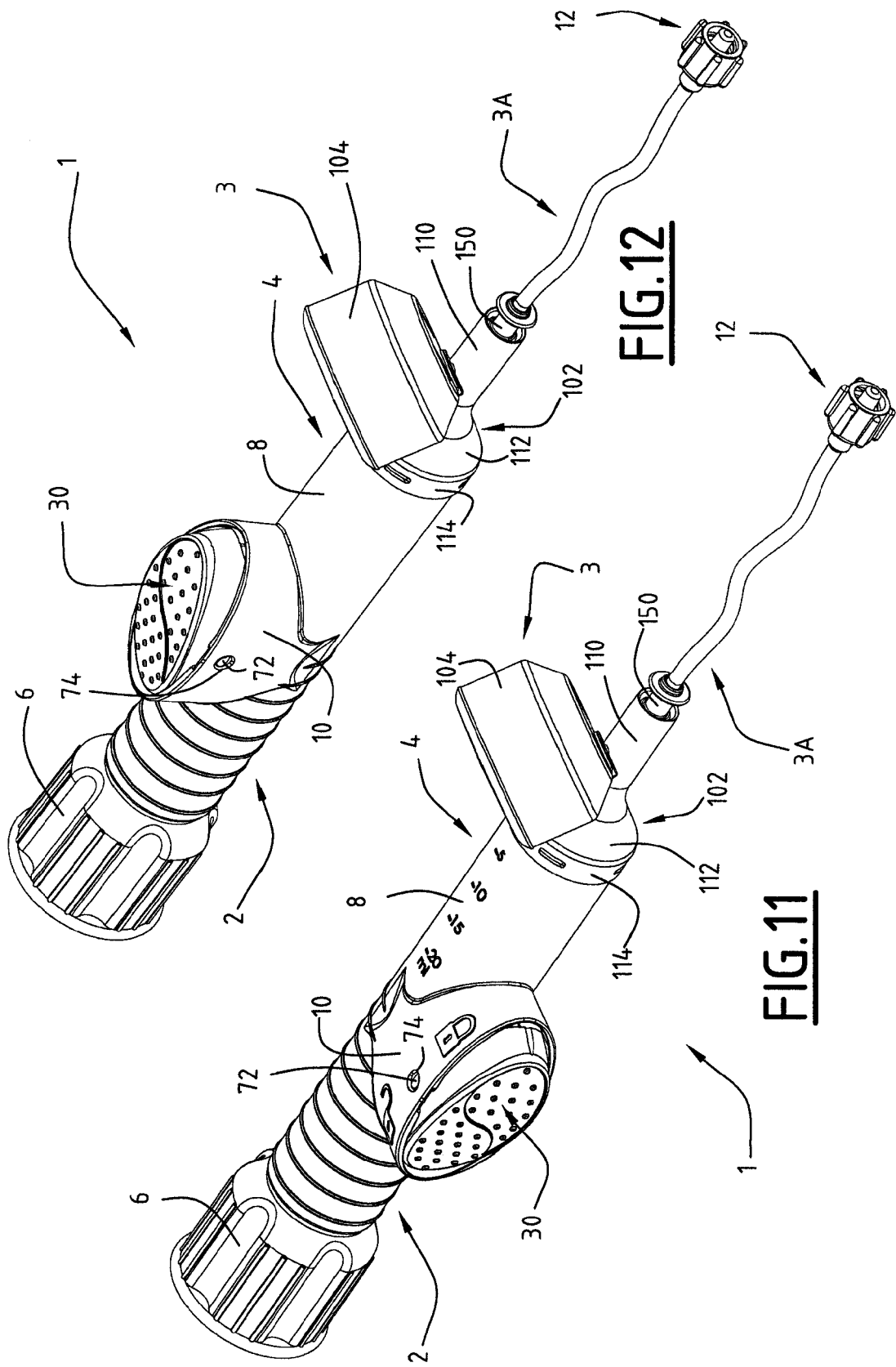

BALLOON INFLATION DEVICE

The present invention concerns a balloon inflation device, of the type comprising a syringe having a syringe barrel and a syringe piston slidably and rotatably movable in said syringe barrel, the piston having exterior threading on at least a section of its length, the syringe barrel further comprising a retractable mechanism for the retention of the piston in the syringe barrel, which mechanism is switchable between a retracted state in which the piston is free to slide in the syringe barrel and an active state in which the free sliding of the piston is impossible and in which the piston can be screwed or unscrewed in the syringe barrel, the device comprising a pressure gauge for measuring the output pressure of the syringe barrel.

Such inflation devices are used to inject fluid into a balloon previously arranged in a contracted state inside an artery or a vein of a patient. Such devices are described for example in document U.S. Pat. No. 5,147,300 or document FR-2 850 286.

These devices are used in particular for percutaneous transluminal angioplasties, in order to dilate the artery or the vein in which the balloon is placed. They can also be used for other applications.

Inflation devices must be capable of providing high pressure, on the order of 30 bars, this pressure being monitored on the pressure gauge provided for this purpose on the device. Under the action of this pressure, the half-nut cooperating with the threading should be held firmly in the hand of the operator, and the operator should screw the piston with the other hand. This handling requires that the operator be able to hold the barrel of the device in their hand in such a way that is comfortable for them. Thus, some operators choose to hold the device in such a way that the piston release member is below the thumb while others choose to hold it in a way that the member is below the index finger. Some positions make seeing the pressure gauge difficult.

A purpose of the invention is to provide a balloon inflation device which has an improved ergonomic design for handling by means of improved visibility of the pressure gauge.

To this end, the invention concerns a balloon inflation device of the abovementioned type, characterized in that the pressure gauge is mounted angularly movable relative to the syringe barrel and around the axis of the syringe barrel.

According to other characteristics of this device, taken individually or in any technically possible combination:
the device comprises a cap delimiting a through-conduit into which a pressure intake opens, the pressure gauge being connected to the output of the pressure intake, and the cap is mounted movable in rotation around the syringe barrel;
the device comprises an O-ring arranged between the cap and the syringe barrel;
the cap is elastically engaged around the syringe barrel;
the syringe barrel comprises a generally cylindrical trunk extended by a neck with an outside diameter less than that of the trunk, and the cap includes a skirt engaged at least partially around the trunk;
the device comprises end stops for the pressure gauge with respect to the syringe barrel limiting the angular movement of the pressure gauge to approximately 90°;
the device comprises a pressure module in which the pressure gauge is integrated, which pressure module is mounted angularly movable relative to the syringe barrel, and around the syringe barrel, and it further comprises an outlet tube connected to the pressure module by a rotary end cap free in rotation with respect to the pressure module;
the syringe barrel further comprises a retractable mechanism for retaining the piston in the syringe barrel, which mechanism is switchable between a retracted state in which the piston is free to slide in the syringe barrel and an active state in which the free sliding of the piston is impossible and in which said piston can be screwed or unscrewed in the syringe barrel;
the device comprises a pressure gauge for measuring the output pressure of the syringe barrel;
the pressure gauge is angularly mounted relative to the syringe barrel and around the axis of the syringe barrel;
the retaining mechanism comprises, for the half-nut, at least one elastically deformable element, bearing on the corresponding half-nut and the on syringe barrel; and
the control member comprises at least one projection bearing on the corresponding half-nut, fitted so as to bear, during the movement of the control member, against two surfaces held by the half-nut and offset from one another in a direction radial to the syringe barrel, the half-nut being in its position separated from the threading while the projection bears against surface radially closest to the syringe piston and the half-nut being in its position in contact with the threading when the projection bears against the surface farthest away.

The invention will be better understood from reading the description that follows, given solely by way of example and by referring to the drawings of which:

FIGS. 11 and 12 are views in perspective of the device in FIG. 1, with its pressure gauge in two different positions.

Figure 1:
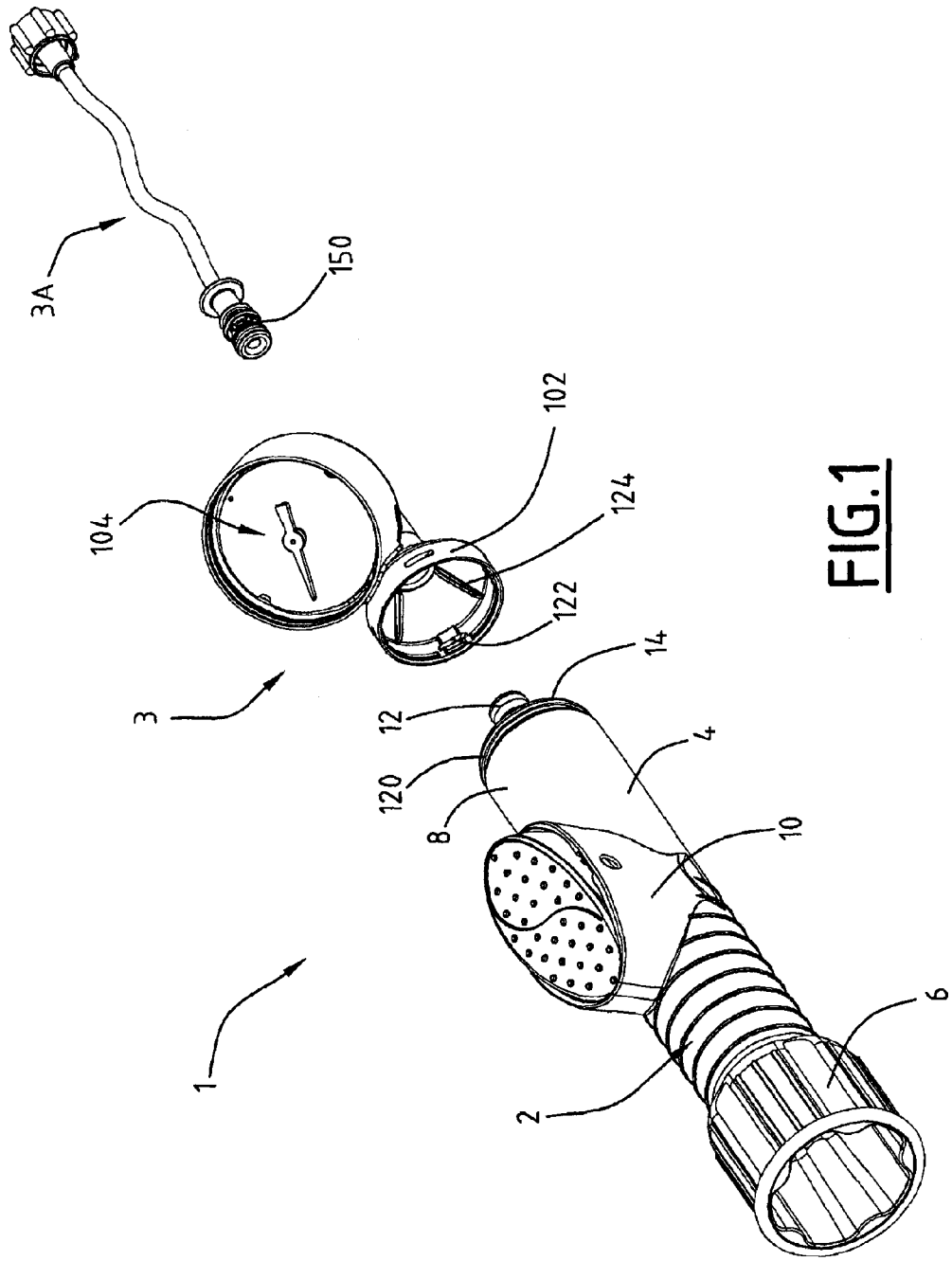
FIG. 1 is a partially exploded view in perspective of the device.

The balloon inflation device 1 shown in FIGS. 1, 2, 3, 4, 5, comprises a syringe 2, a pressure measuring module 3 and a tube 3A.

The syringe 2 extends along an axis X-X and essentially comprises a syringe barrel 4 and a piston 6. The syringe advantageously has a capacity of 20 cm$^3$.

The syringe barrel 4, made of transparent plastic, comprises a trunk 8 from which a side housing 10 integrally formed from the material of the trunk protrudes. The housing 10 is open.

The front end of the syringe barrel has a neck 12 of smaller diameter provided at the end of a converging section 14 extending the trunk. This fastening assembly comprises a deformable device 14 for retaining the connector and the sealing means 16 formed for example by a gasket.

The syringe piston 6 is formed by a rod 20 fitted at its end inside the trunk 8, through the back end of the syringe barrel 4, with a head 22 equipped with a gasket 23 which slides sealably inside the syringe barrel 4. The rod has, at its other end, a handle 24 intended for the manual actuation of the piston 6. This handle is equipped with a grip 26 to facilitate handling.

The rod 20 is provided with exterior threading 28 on at least a section of its length.

The device 1 also comprises a piston 6 retention mechanism 30, received essentially inside the side housing 10, as depicted in FIGS. 4, 5, 8 and 9 in particular.

The retaining assembly 30 comprises a half-nut 32 with a hollow body 34, depicted in greater detail in FIGS. 4, 5, 6, 8 and 9. This body is essentially formed by a bottom wall 36 which extends parallel to the syringe piston 6, two opposite transversal walls 38 which extend essentially perpendicularly to the axis X-X of the syringe, and two opposite lateral walls 40 which connect the walls 38, only one of these walls 40 being visible in FIGS. 4, 5, 6, 8 and 9.

Figure 10:
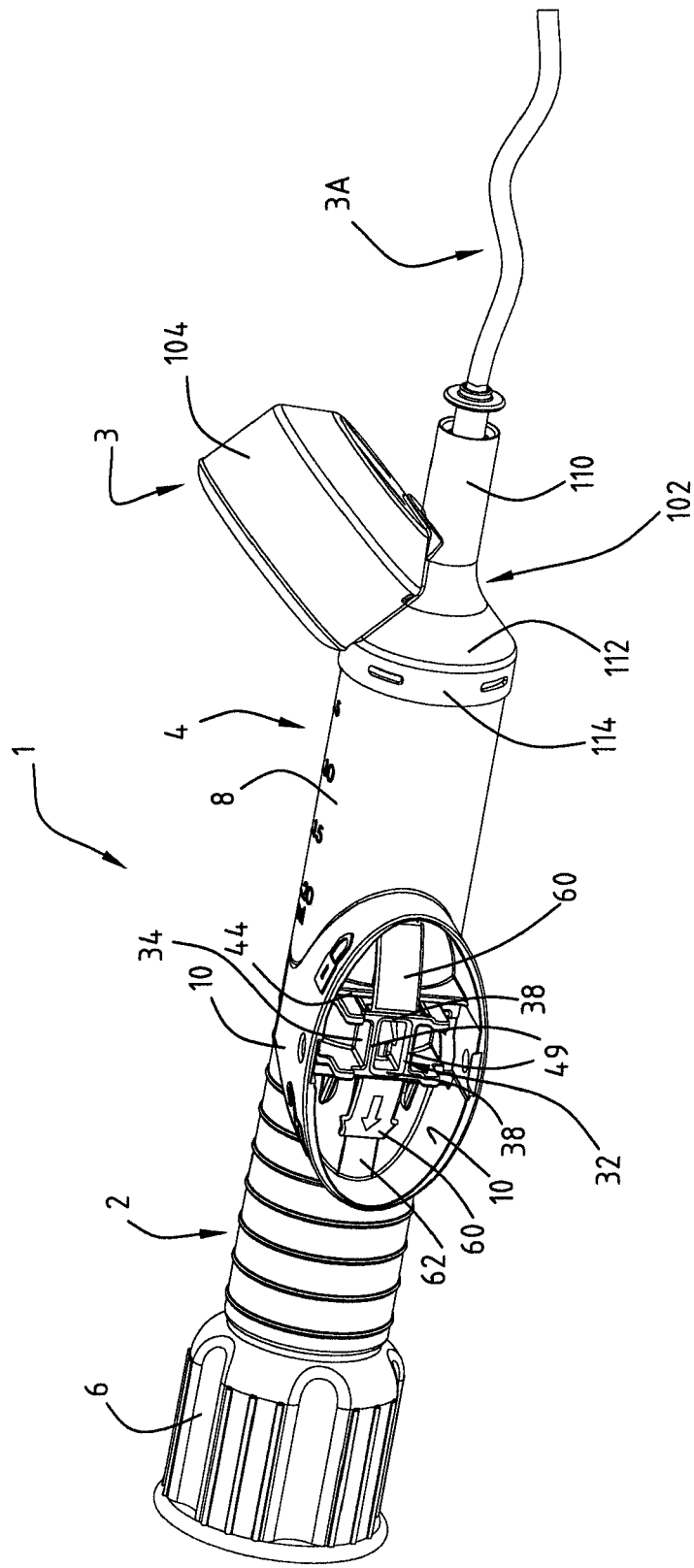
FIG. 10 is a view in perspective of the device in FIG. 4, the control member for the movement of the half-nut not being represented.

The half-nut 32 is received inside an oblong through-opening 42 made in the trunk 8 of the syringe barrel 4, and is held there by a housing bracket 44 attached to the syringe barrel 4, for example integrally formed of the material of the trunk 8 and the housing 10 as depicted in FIG. 10. Said bracket 44 is ribbed, on the one hand, in such a way as to allow the movement of the half-nut in a direction essentially perpendicular to the axis X-X and contained in the section plane of FIG. 4, and, on the other hand, to block the half-nut both in the other directions perpendicular to the axis X-X as well as parallel to this axis.

The bottom wall 36 of the half-nut 32 has, on the side facing the interior of the syringe barrel 4, a threaded surface 46 intended to come into contact with the threading 28 of the piston 6.

Figure 2:
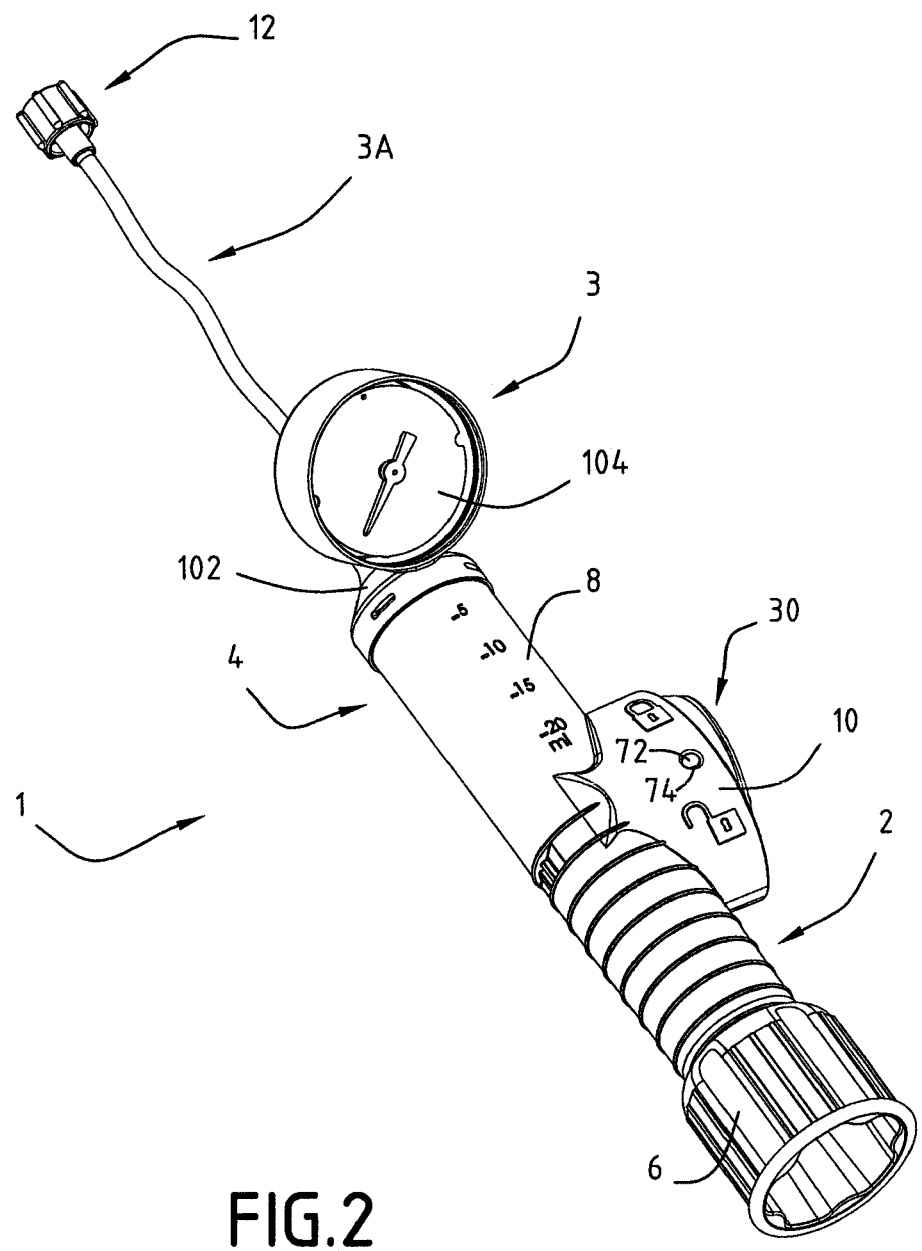
FIGS. 2 and 3 are perspective views of the device according to the invention, in the configurations allowing the sliding of the syringe piston and the screwing/unscrewing of the piston, respectively.
Figure 3:
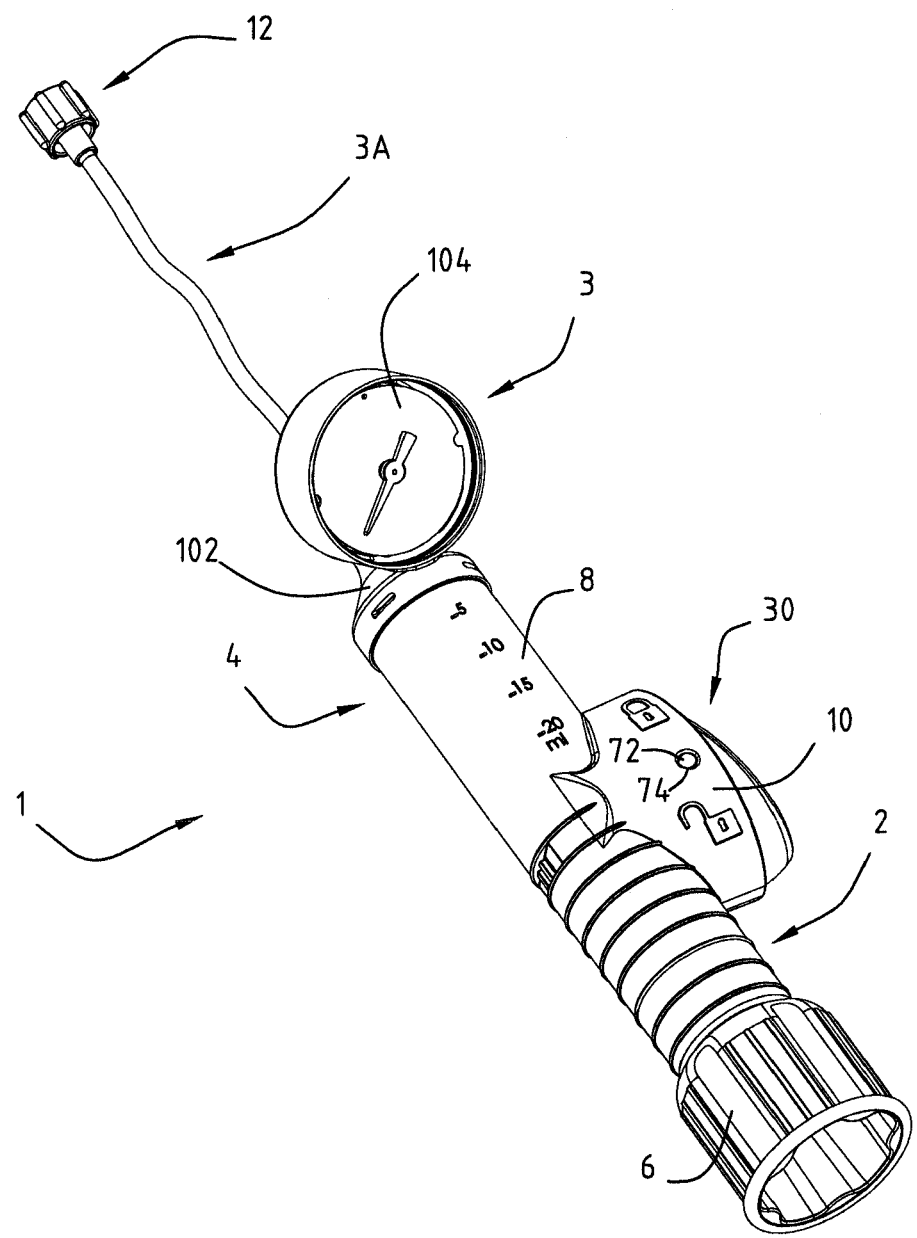
Figure 8:
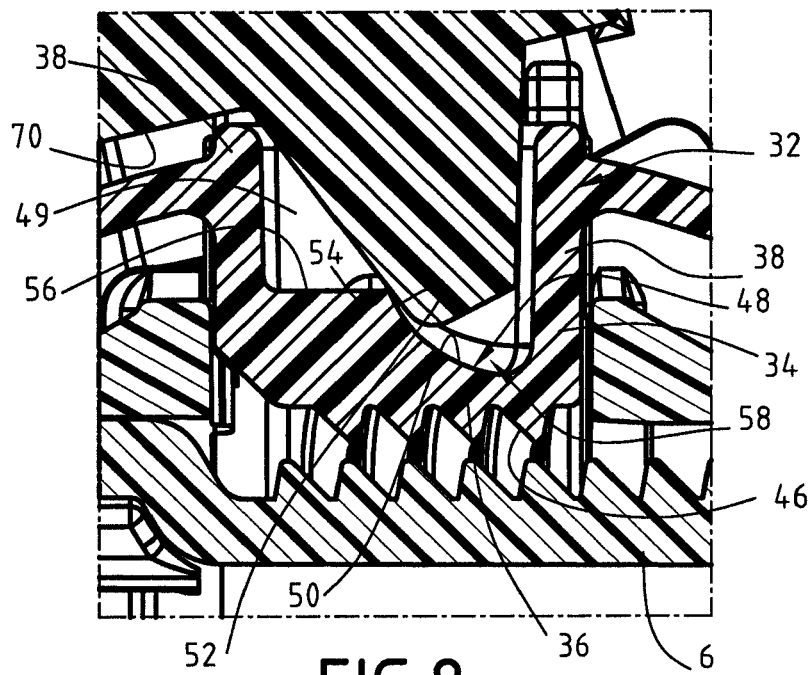
FIGS. 8 and 9 are larger scale views of the detail of the cooperation of the half-nut and the control member in the configurations which allow the sliding of the piston and the screwing/unscrewing of the piston respectively.
Figure 9:
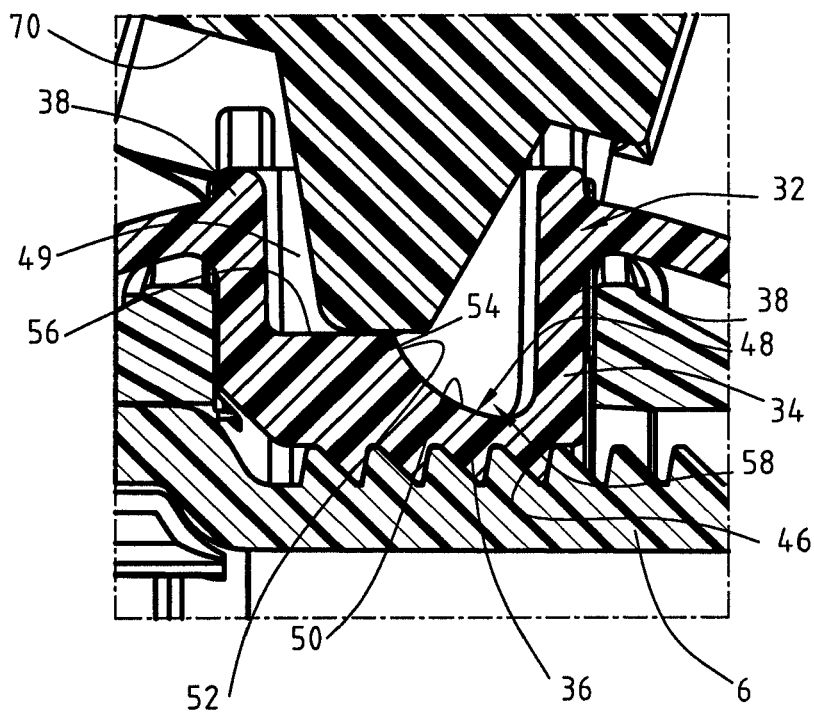

The half-nut is thus movable between a position separated from the threading 28, depicted in FIGS. 2, 4, 5 and 8, in which the piston 6 is free to slide inside the syringe barrel 4, and a position in contact with this threading, depicted in FIGS. 3 and 9, in which the piston 6 can be screwed or unscrewed in the syringe barrel 4, its free sliding being impossible.

The bottom wall 36 of the half-nut 32 also has, on the side directed towards the exterior of the syringe barrel 4, a stepped surface 48, depicted in detail in FIGS. 8 and 9. This surface is bordered by two longitudinal panels 49. It comprises in succession, from back to front, a first essentially flat surface 50 (not depicted in FIG. 6), a surface inclined outward forming a ramp 52, a neck 54 projecting outward, and, set back toward the interior in relation to the top of the neck 54, a second essentially flat surface 56, which is farther away from the axis of the syringe than the first surface 50. In FIGS. 8 and 9, the respective proportions for surfaces 50, 52 and 56 and of the neck 54 have been exaggerated for better visibility.

Similarly, the opposite lateral walls 40 have on their upper area a succession of two flat surfaces 58A and 58B on their top sides, made at different levels connected by an intermediary cam surface 58C. These surfaces are made essentially according to the same general profile as the surfaces 50, 56 and 52 respectively.

The retention assembly 30 also comprises two elastically deformable tabs 60 which extend from either side of the half-nut 32. These tabs 60 are integrally formed from the material of the lateral walls 38 of the body 34 of the half-nut.

The free ends of these tabs bear elastically along the length of the trunk 8 of the syringe barrel.

A support shim 64 for the rod 20 is arranged opposite the half-nut 32 between the inside wall of the syringe barrel and the rod 20 opposite the half-nut 32 with respect to the axis of the rod.

Figure 4:
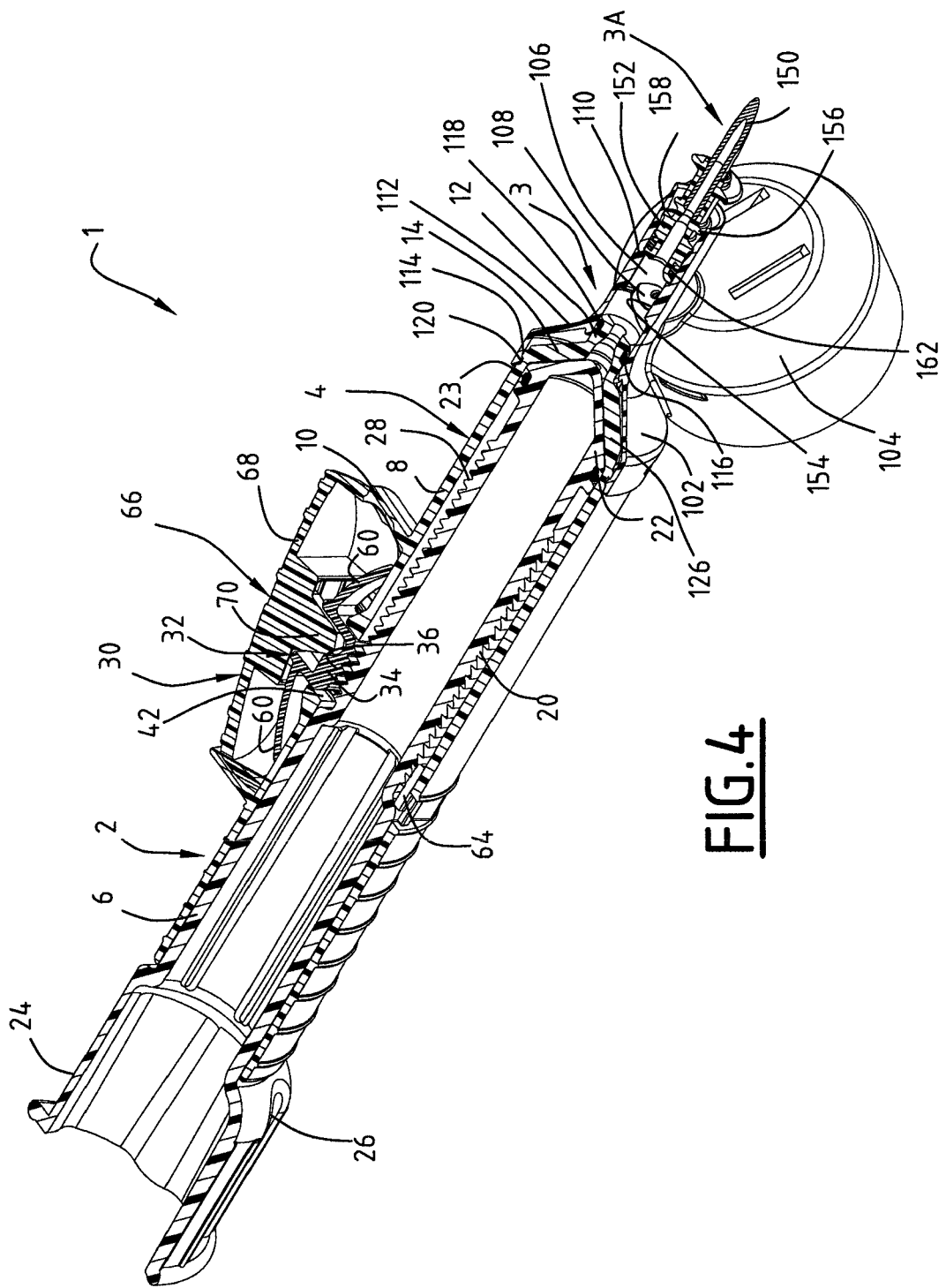
FIG. 4 is a view in perspective and in longitudinal section along a median plane of the device in FIG. 2.
Figure 5:
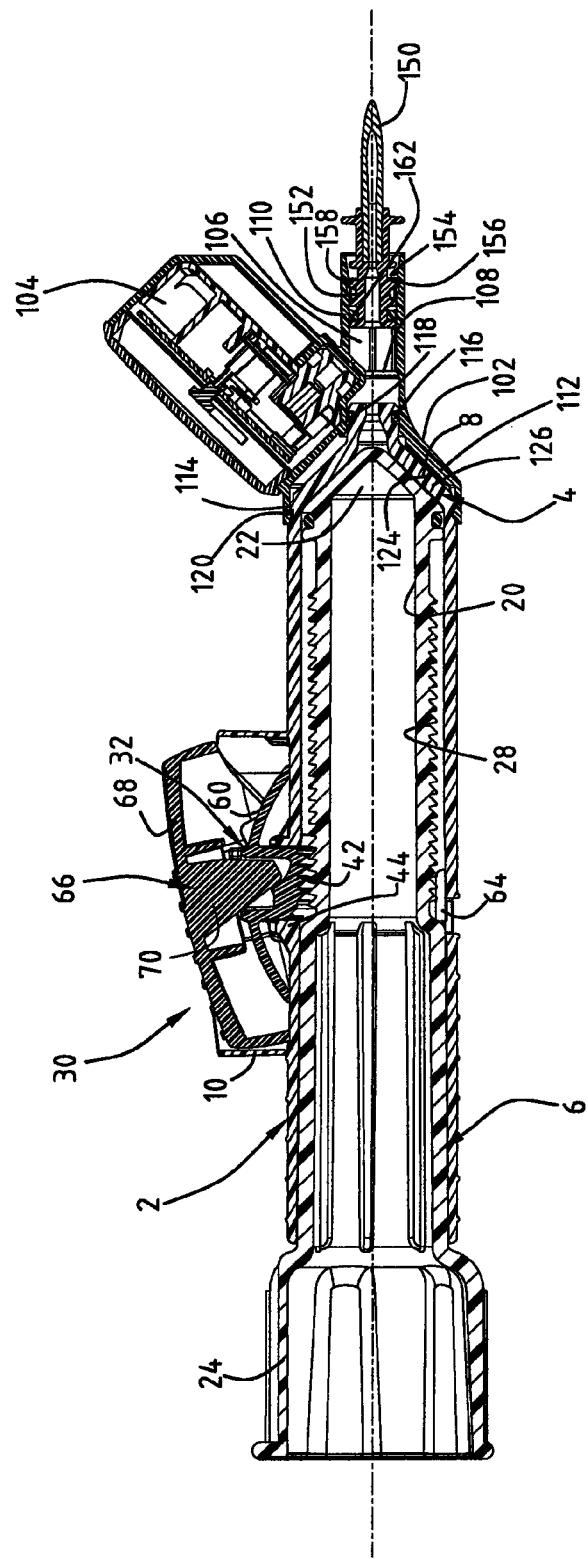
FIG. 5 is a top cross-sectional view along the same plane as the section in FIG. 4 of the device in FIG. 2.
Figure 6:
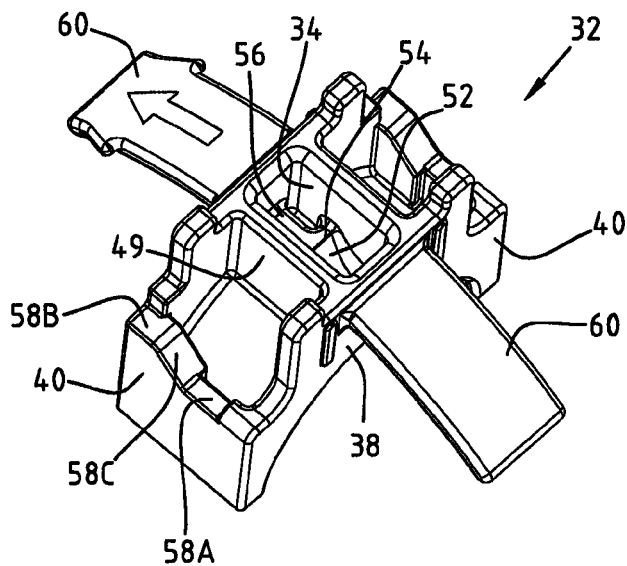
FIG. 6 is a larger scale view in perspective of a half-nut contained in the device.
Figure 7:
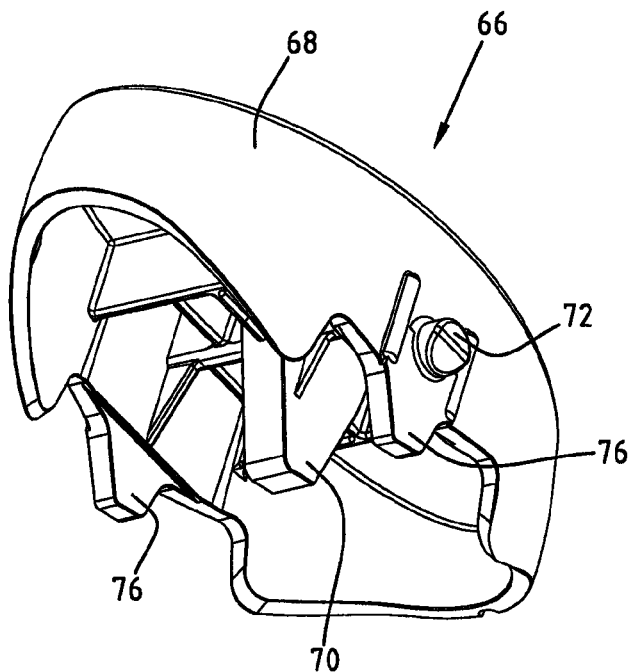
FIG. 7 is a larger scale view in perspective of the control member of the half-nut.

The retention assembly 30 further comprises, as depicted in FIGS. 4, 5 and 7, a member 66 for controlling the movement of the half-nut 32, made entirely from plastic and molded. This member is formed from a half shell 68 the inner recess of which is turned towards the syringe barrel 6, and a projection 70, which is generally pyramidal in shape and the base of which is integrally formed of the material of the half shell.

The half shell 68 forms a top cover for the corresponding housing 10, and is movable in relation to the latter. More specifically, as depicted in FIGS. 2 and 3, two cylindrical pins 72 (only one can be seen in FIGS. 2 and 3), whose axis is perpendicular to the section plane of FIGS. 4 and 5, protrude in relation to the half shell 68, each pin extending from one of the two sides of the half shell essentially parallel to the section plane in FIG. 4. These pins are received in the openings 74 essentially arranged complementary to one another in the wall of the housing 10. In this way, the control member 66 can be pivoted around the axis of the pins relative to the syringe barrel 4.

The projection 70 is fitted so as to be received inside the hollow body 34 of the half-nut 32 and to bear on the stepped surface 48 of the half-nut.

In a corresponding way, the protruding projections 76 are formed by each side of the half shell 68 and are suitable for cooperating with surfaces 58A, 58B, and 58C made on the lateral walls 40 of the half-nut.

More specifically, when the control member 66 is pivoted backwards, as depicted in FIGS. 1, 4, 5, and 8, the free end of the projection 70 bears against the surface 50 and the projections 76 bear on the surfaces 58A of the elastic tabs 60 holding the half-nut in a separated position, such that the piston 6 is free to slide.

When the member 66 is pivoted forward, as depicted in FIGS. 3 and 9, the projection 70 bears on the surface 56, while the projections 76 bear on the surfaces 58B. The elastic tabs 60 are thus deformed, such that the half-nut 32 is in contact with the threading 28 of the piston to allow only the screwing or unscrewing of the piston.

The movements of the projection 70 are guided, and potentially limited, by the inner surfaces of walls 38 and 49 of the hollow body 34. For example, for the depicted device, the pivot angle of the projection is on the order of 120 in relation to the axis of the syringe.

The pressure measuring module 3 essentially comprises a support cap 102 mounted on the syringe barrel 4 and a pressure gauge 104 held rigidly by the cap 102. The pressure gauge is of any suitable type and is for example a mechanical pressure gauge with needle, or an electronic pressure gauge.

The cap 102 delimits a conduit 106 visible in FIGS. 4 and 5, in which a pressure intake 108 opens, to the output of which the pressure gauge 104 is connected.

The cap 102 has a general funnel shape with a generally cylindrical nose 110 connected by a tapered section 112 to a skirt 114 around the end of the trunk 8.

The neck 12 is equipped, in a groove 116, with an O-ring 118 providing a seal between the syringe barrel and the cap 102.

In addition, at its end, the trunk 8 of the syringe barrel has a peripheral groove 120 suitable for receiving four protrusions 122 made on the inside surface of the skirt 114. The protrusions 122 are angularly separated by 90° at the periphery of the skirt and provide guidance in rotation of the cap 102 around the axis of the trunk 8. During assembly, the protrusions 122 are elastically engaged around the syringe barrel in the groove 120.

Inside the tapered section 118 of the cap there are axial ribs 124 angularly spaced at 90°. These ribs can be seen in FIGS. 1 and 5. In addition, the end stops 126 which can be seen in FIG. 4 are provided on the outside of the convergent section 14. These stops are suitable for cooperating with the ribs 124 to allow the angular movement of the cap in relation to the syringe barrel on a maximum path of approximately 90°.

The cap 120 is press-fitted on by elastic interlocking around the syringe barrel 8, the protrusions 122 being received in the groove 120.

The tube 3A comprises a flexible conduit 150 equipped, at a first free end, with end fitting 152 rotatably mounted in a counterbore 154 of the conduit 106 formed at the free end of the nose 110. This counterbore 154 has a groove 156 in which a flange 158 of the end fitting 152 is received to allow the axial holding of the end fitting in the conduit. An O-ring 162 or any other sealing system is provided in the end fitting 152 between the end fitting and the inner surface of the conduit 106 to allow the guiding of the fluid from the syringe barrel to the tube 150 through the conduit 106.

With the design of such a device, the pressure gauge 104 can be placed in two positions relative to the syringe barrel that are angularly offset at 90°, as depicted in FIGS. 11 and 12, in such a way that the pressure gauge is either in the same plane as that of the retaining assembly 30, as depicted in FIG. 12, or in a plane angularly offset by 90° from the plane of the retaining assembly 30 around the axis of the syringe, as illustrated in FIG. 11. Thus, whatever the method of handling the tool, whether the handle is actuated by the palm of the hand or the fingers, the operator can, depending on the position of the pressure gauge, see the pressure gauge with ease in order to read the pressure.

Finally, the presence of the rotary connection between the tube 3A and the rest of the device allows for reduced production costs, since the rotary connection formed between the cap 102 and the tube 150 obviates the need for providing a rotary connection for the other end of the tube 150. The position of the rotary connection makes it possible to assemble the syringe and tube at the end of assembly of the device.

The operation of the inflation device 1 is as follows:

To inflate a balloon, the operator connects, for example by means of a tube fitted with a connector at its upstream, the front end of the device 1 to a balloon, by attaching the connector to the assembly 12.

The operator then grips the device by manually pressing, particularly between the thumb and the index finger, the rear part of the half shell 68, pivoting the control member 66 backwards. The operator can also press the piston rod inside the syringe barrel 4 in order to increase the pressure of the fluid contained in the syringe, until the pressure reaches approximately 3 bars, which corresponds in general to the pressure which can be obtained by simply pressing the piston.

After this, the operator pivots the control member 66 forward by putting manual pressure on the front section of the control member 66. The pivoting of the control member forward causes the end of the projection 70 to move from the surface 50 to the surface 56. Said end then bears on the ramp 52 during movement, causing, by cam effect, the engagement of the threading 28 with the half-nut 32.

The operator continues putting on pressure by progressively screwing the piston into the syringe barrel until, for example, 30 bars of pressure is reached. The half-nut 32 is firmly held in contact with the threading of the piston by projection 70, the neck 54 of the support surface 48 of the half-nut ensuring the blockage of the control members when in a pivoted backwards position.

The release of the half-nut is carried out next by repeating the abovementioned steps in reverse.

During the operation of the device and particularly during the use of the control member 30, the movement of the projection 70 is accompanied by the corresponding movement of the projections 76 along the surfaces 58A, 58B and 58C. Thus, the action of projection 70 is reinforced by the simultaneous action of the projections 76. Because the three projections are distributed along the articulation axis of the control mechanism 30, they ensure good stability of this member and efficiently and reliably maintain the half-nut in contact with the threading for retaining the piston, even if the piston exerts significant transversal force on the half-nut while it is being screwed.

In the syringe described here, the presence of the shim 64 facing the symmetrically arranged half-nut 32 prevents any bending of the rod 20 of the piston 6 and the correct retention of the rod by the half-nut 32.

Furthermore, the engagement and disengagement of the half-nut with the threading 28 of the piston 6 are caused by the pivoting of the control member 66 by ergonomically gripping the device with one's hand.

The invention claimed is:

1. A balloon inflation device comprising a syringe (2) having a syringe barrel (4) and a syringe piston (6) slidably and rotatably movable in said syringe barrel (4), the piston (6) having exterior threading (28) on at least a section of its length, the syringe barrel further comprising a retractable mechanism (30) for the retention of the piston (6) in the syringe barrel, which mechanism (30) is switchable between a retracted state in which the piston (6) is free to slide in the syringe barrel and an active state in which the free sliding of the piston (6) is impossible and in which the piston (6) can be screwed or unscrewed in the syringe barrel (4), the device further comprising a pressure gauge (104) for measuring the output pressure of the syringe barrel (4)

wherein the pressure gauge (104) is mounted movable relative to the syringe barrel (4), such that the pressure gauge rotates around a surface of the syringe barrel (4), and wherein the device comprises a cap (102) delimiting a through-conduit (106) into which a pressure intake (108) opens, the pressure gauge (104) being connected to the output of the pressure intake, and in that the cap (102) is mounted movable in rotation around the syringe barrel (4).

2. The device according to claim 1, wherein the device comprises an O-ring (23) arranged between the cap (102) and the syringe barrel (4).

3. The device according to claim 1, wherein the cap (102) is elastically engaged around the syringe barrel (4).

4. The device according to claim 1, wherein the syringe barrel (4) comprises a generally cylindrical trunk (8) extended by a neck (12) the outside diameter of which is less than that of the trunk (8), and in that the cap (102) comprises a skirt (114) engaged at least partially around the trunk (8).

5. The device according to claim 1, wherein the device comprises end stops (126) for the pressure gauge (104) with respect to the syringe barrel (4) limiting the movement of the pressure gauge to essentially 90°.

6. The device according to claim 1, wherein the device comprises a pressure module (3) in which the pressure gauge (104) is integrated, which pressure module (3) is mounted movable relative to the syringe barrel (4), and around the syringe barrel (4), and in that it further comprises an outlet tube (3A) connected to the pressure module (3) by a rotary end cap (152) free in rotation with respect to the pressure module (3).

7. A balloon inflation device comprising a syringe (2) having a syringe barrel (4) and a syringe piston (6) slidably and rotatably movable in said syringe barrel (4), the piston (6) having exterior threading (28) on at least a section of its length, the syringe barrel further comprising a retractable mechanism (30) for the retention of the piston (6) in the syringe barrel, which mechanism (30) is switchable between a retracted state in which the piston (6) is free to slide in the syringe barrel and an active state in which the free sliding of the piston (6) is impossible and in which the piston (6) can be screwed or unscrewed in the syringe barrel (4), the device comprising a pressure gauge (104) for measuring the output pressure of the syringe barrel (4)

wherein the pressure gauge (104) is mounted movable relative to the syringe barrel (4), such that the pressure gauge rotates around a surface of the syringe barrel (4), wherein the retractable retaining mechanism (30) comprises:
  at least a half-nut (32),
  at least one elastically deformable element (60), bearing on the corresponding half-nut and the on syringe barrel (4), and
  at least a control member (66) for controlling the movement of the half nut, comprises at least one projection (70) bearing on the corresponding half-nut (32), fitted so as to bear, during the movement of the control member, against two surfaces (50) of the half-nut and offset from one another in a direction radial to the syringe barrel (4), the half-nut being in its position separated from the exterior threading while the projection bears against the surface (50) radially closest to the syringe piston (6) and the half-nut being in it position of contact with the exterior threading when the projection bears against the surface (56) farthest away.

8. The device according to claim 7, wherein:
the half-nut has a hollow body having a bottom wall which extends parallel to the syringe piston,
the bottom wall has a side directed towards the exterior of the syringe barrel, having a stepped surface bordered by two longitudinal panels,
the stepped surface comprises in succession, a first flat surface, a surface inclined outward forming a ramp, a neck projecting outward, and, set back toward the interior in relation to the top of the neck, a second flat surface, which is farther away from the axis of the syringe than the first surface.

9. The device according to claim 6, wherein:
the device comprises a cap delimiting a through-conduit into which a pressure intake opens, the pressure gauge being connected to the output of the pressure intake, and the cap being mounted movable in rotation around the syringe barrel,
the through-conduit of the cap has a counterbore having a groove,
the outlet tube comprises a flexible conduit having a first free end equipped with an end fitting rotatably mounted in the counterbore, said end fitting having a flange received in the groove to allow the axial holding of the end fitting in the through-conduit.

\* \* \* \* \*